(12) United States Patent
McManus et al.

(10) Patent No.: US 8,456,634 B2
(45) Date of Patent: Jun. 4, 2013

(54) OPTICAL INTERROGATION SENSORS FOR COMBUSTION CONTROL

(75) Inventors: Keith Robert McManus, Clifton Park, NY (US); Lewis Berkley Davis, Jr., Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 839 days.

(21) Appl. No.: 12/484,466

(22) Filed: Jun. 15, 2009

(65) Prior Publication Data

US 2010/0313572 A1    Dec. 16, 2010

(51) Int. Cl.
 *G01N 21/00* (2006.01)

(52) U.S. Cl.
 USPC ............... 356/436; 60/772; 60/773; 60/39.5; 60/39.24; 356/432; 356/437

(58) Field of Classification Search
 USPC .............. 60/773, 39.001, 39.11, 793, 39.3, 60/39.21, 39.22, 39.24, 39.25, 39.26, 39.27, 60/39.281, 39.282, 794, 795; 356/326, 327, 356/432, 436, 437; 92/5 R; 91/1; 250/342, 250/339.15, 340, 353, 372; 340/500, 513, 340/578, 600
 See application file for complete search history.

(56) References Cited

U.S. PATENT DOCUMENTS

| | | | |
|---|---|---|---|
| 3,899,878 A * | 8/1975 | Compton et al. | .......... 60/39.281 |
| 4,060,980 A | 12/1977 | Elsaesser et al. | |
| 4,074,104 A | 2/1978 | Fulkerson | |
| 4,630,927 A | 12/1986 | Fulkerson | |
| 4,639,598 A | 1/1987 | Kern et al. | |
| 4,691,196 A | 9/1987 | Kern et al. | |
| 4,695,721 A | 9/1987 | Fulkerson et al. | |
| 4,701,624 A | 10/1987 | Kern et al. | |
| 4,771,182 A | 9/1988 | Fulkerson | |
| 5,162,658 A * | 11/1992 | Turner et al. | .................. 250/554 |
| 5,257,496 A * | 11/1993 | Brown et al. | .................... 60/773 |
| 5,286,947 A | 2/1994 | Clyde et al. | |
| 5,332,386 A * | 7/1994 | Hosome et al. | .................. 431/12 |
| 5,349,850 A | 9/1994 | Young | |
| 5,384,467 A | 1/1995 | Plimon et al. | |
| 5,394,005 A | 2/1995 | Brown et al. | |
| 5,467,185 A | 11/1995 | Engeler et al. | |
| 5,544,478 A | 8/1996 | Shu et al. | |
| 5,578,828 A * | 11/1996 | Brown et al. | ................. 250/342 |
| 5,589,682 A | 12/1996 | Brown et al. | |
| 5,608,515 A | 3/1997 | Shu et al. | |
| 5,659,133 A | 8/1997 | Sims et al. | |

(Continued)

FOREIGN PATENT DOCUMENTS

| | | |
|---|---|---|
| EP | 1108956 A2 | 6/2001 |
| JP | 11-166722 A | 6/1999 |
| JP | 2009-103630 A | 5/2009 |

*Primary Examiner* — William H Rodriguez
*Assistant Examiner* — Craig Kim
(74) *Attorney, Agent, or Firm* — Sutherland Asbill & Brennan LLP

(57) ABSTRACT

Certain embodiments of the invention may include systems and methods for providing optical interrogation sensors for combustion control. According to an example embodiment of the invention, a method for controlling combustion parameters associated with a gas turbine combustor is provided. The method can include providing an optical path through the gas turbine combustor, propagating light along the optical path, measuring absorption of the light within the gas turbine combustor, and controlling at least one of the combustion parameters based at least in part on the measured absorption.

20 Claims, 3 Drawing Sheets

U.S. PATENT DOCUMENTS

| | | |
|---|---|---|
| 5,755,819 A | 5/1998 | Bonanni et al. |
| 5,978,525 A | 11/1999 | Shu et al. |
| 6,135,760 A | 10/2000 | Cusack et al. |
| 6,158,261 A | 12/2000 | Utyashev et al. |
| 6,239,434 B1 | 5/2001 | Brown |
| 6,350,988 B1 | 2/2002 | Brown |
| 6,473,705 B1 | 10/2002 | Conners |
| 6,599,028 B1 | 7/2003 | Shu et al. |
| 6,621,060 B1 | 9/2003 | Nantel et al. |
| 6,646,265 B2 | 11/2003 | Brown et al. |
| 6,710,878 B1 | 3/2004 | Dean et al. |
| 6,775,986 B2 | 8/2004 | Ganz et al. |
| 6,784,430 B2 | 8/2004 | Matocha et al. |
| 6,818,897 B2 | 11/2004 | Brown |
| 6,838,741 B2 | 1/2005 | Sandvik et al. |
| 6,978,074 B2 | 12/2005 | Shu et al. |
| 7,002,156 B2 | 2/2006 | Sandvik et al. |
| 7,005,645 B2 | 2/2006 | Von Drasek et al. |
| 7,112,796 B2 | 9/2006 | Brown et al. |
| 7,151,872 B1 | 12/2006 | Xia et al. |
| 7,285,433 B2 | 10/2007 | Kretchmer et al. |
| 7,400,789 B2 | 7/2008 | Xia et al. |
| 7,440,097 B2 | 10/2008 | Benicewicz et al. |
| 7,469,077 B2 | 12/2008 | Xia et al. |
| 7,489,835 B1 | 2/2009 | Xia et al. |
| 2001/0009268 A1 | 7/2001 | Brown et al. |
| 2003/0152307 A1 | 8/2003 | Drasek et al. |
| 2004/0089810 A1 | 5/2004 | Brown et al. |
| 2007/0281260 A1 | 12/2007 | McLellan |
| 2007/0296966 A1 | 12/2007 | Benicewicz et al. |
| 2008/0083228 A1 | 4/2008 | Myhre |
| 2008/0218758 A1 | 9/2008 | Xia et al. |
| 2008/0289342 A1* | 11/2008 | Sappey et al. .......... 60/793 |
| 2009/0017406 A1 | 1/2009 | Farias Fuentes et al. |

\* cited by examiner

OPTICAL INTERROGATION SENSORS FOR COMBUSTION CONTROL

FIELD OF THE INVENTION

This invention generally relates to sensors, and more particularly relates to optical interrogation sensors for combustion control.

BACKGROUND OF THE INVENTION

Modern industrial gas turbines are required to convert energy at a high efficiency while producing minimum polluting emissions. But these two requirements are at odds with each other since higher efficiencies are generally achieved by increasing overall gas temperature in the combustion chambers, while pollutants such as nitrogen oxide are typically reduced by lowering the maximum gas temperature. The maximum gas temperature can be reduced by maintaining a lean fuel-to-air ratio in the combustion chamber, but if the fuel/air mixture is too lean, incomplete fuel combustion can produce excessive carbon monoxide and unburned hydrocarbons. Other operational problems emerge when operating with lean combustion including unstable load transitions and combustion instability, also known as combustion dynamics. Therefore, the fuel/air mixture and the temperature in the reaction zone must be controlled to support complete combustion.

To balance the conflicting needs for increased efficiency and reduced emissions, extremely precise control is required to adjust the fuel/air mixture in the reaction zones of the combustors. Systems have been proposed for controlling the fuel/air mixture by monitoring various combustion parameters, and using the measured parameters as input to control the fuel system. For example, one conventional system includes a control system where fuel flow rates, pressure levels, and discharge exhaust temperature distributions are utilized as input for setting fuel trim control valves.

Other techniques for controlling combustion dynamics include measuring light emission from the combustion burner flame, and using the measured signal to control certain combustion parameters. For example, one conventional system uses a closed loop feedback system employing a silicon carbide photodiode to sense the combustion flame temperature via the measurement of ultraviolet radiation intensity. The sensed ultraviolet radiation is utilized to control the fuel/air ratio of the fuel mixture to keep the temperature of the flame below a predetermined level associated with a desired low level of nitrogen oxides.

Other conventional systems can use optical fibers for gathering and transmitting light from a combustion region to detectors. Yet other conventional systems can use a video camera to capture images of the flame primarily for monitoring the presence or absence of a flame.

Mass flux sensing techniques have been proposed for use in turbines. For example, laser-based Doppler-shift measurement systems may be used for determining air-flow in a turbine air inlet duct, and similar systems have been proposed for measuring the static temperature by comparing the absorption features from two light generators (lasers) of different frequency. A need remains for improved systems and methods for providing optical sensors.

BRIEF SUMMARY OF THE INVENTION

Some or all of the above needs may be addressed by certain embodiments of the invention. Certain embodiments of the invention may include systems and methods for providing optical interrogation sensors for combustion control.

According to an example embodiment of the invention, a method for controlling combustion parameters associated with a gas turbine combustor is provided. The method can include providing an optical path through the gas turbine combustor, propagating light along the optical path, measuring absorption of the light within the gas turbine combustor, and controlling at least one of the combustion parameters based at least in part on the measured absorption.

According to another example embodiment, a system for controlling combustion parameters associated with a gas turbine combustor is provided. The system can include at least one photodetector in communication with an optical path through the gas turbine combustor, a light source operable to propagate light along the optical path to the at least one photodetector, and a control device operable to control at least one of the combustion parameters based at least in part on one or more signals from the one or more photodetectors.

According to another example embodiment, a gas turbine is provided. The gas turbine can include a combustor, at least one photodetector in communication with an optical path through the combustor, a light source operable to propagate light along the optical path to the at least one photodetector, and at least one control device operable to control one or more combustion parameters based at least in part on one or more signals from the at least one photodetector, wherein the one or more signals comprise at least an absorption signal.

Other embodiments and aspects of the invention are described in detail herein and are considered a part of the claimed invention. Other embodiments and aspects can be understood with reference to the description and to the drawings.

BRIEF DESCRIPTION OF THE FIGURES

Reference will now be made to the accompanying drawings, which are not necessarily drawn to scale, and wherein.

DETAILED DESCRIPTION OF THE INVENTION

Embodiments of the invention will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

An embodiment of the invention may enable combustion parameters to be measured in a turbine combustor by probing or interrogating the combustor with light to detect the temporal and/or spectral attenuation of the light after it has passed through the regions of interest. According to embodiments of the invention, the measured combustion parameters may in turn be utilized to control various parameters of the combustor, including, but not limited to fuel flow rates, fuel/air ratios, and fuel flow distributions to optimize nitrous oxide emissions, dynamic pressure oscillations, and fuel efficiencies.

According to example embodiments, specific chemical species may be monitored and controlled within the combustor by utilizing the principle of light absorption. According to an example embodiment, light that is launched through a combustor may be measured to determine the presence and concentration of certain chemical species within the combustor via the spectral and/or temporal attenuation of the light. According to example embodiments, the spectrum-resolved light absorption may be used to identify chemical species including $H_2O$, $CH_4$, CO, $CO_2$, $C_2$, CH, OH and NO. The measured signals may be correlated with the fuel-to-air ratio, heat release rate, and temperature. According to example embodiments, the time-resolved output from optical detectors may be analyzed to reveal unsteady phenomena associated with the combustion, and may be used to indicate combustion-acoustic oscillations (combustion dynamics). In addition, the output signals may be used as feedback for use in a closed-loop combustion control system. Various sensor options and configurations for combustion control applications, according to embodiments of the invention, will now be described with reference to the accompanying figures.

Figure 1:
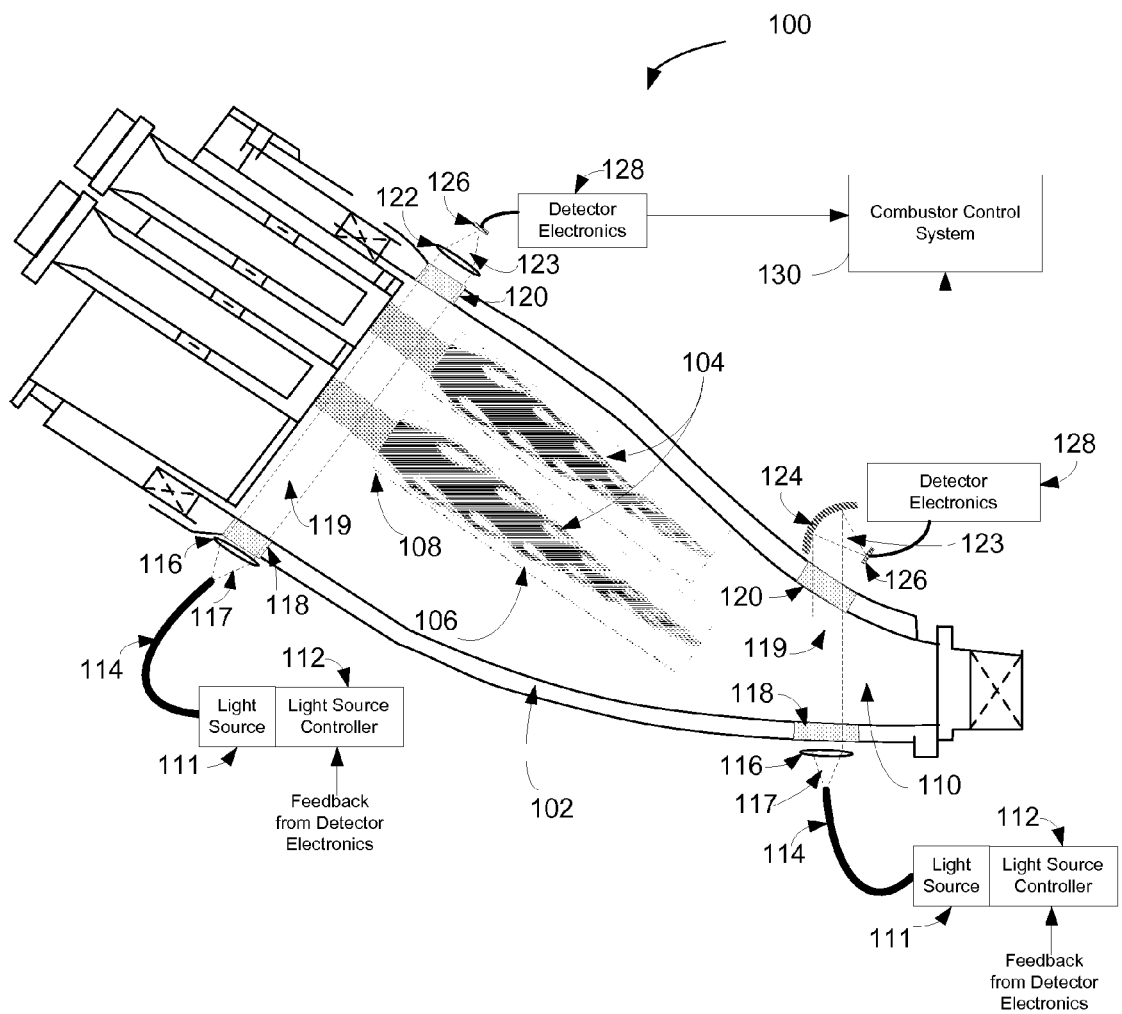
FIG. 1 depicts illustrative optical interrogation systems in communication with the turbine combustor, according to an example embodiment of the invention.

FIG. 1 illustrates an example can combustor with interrogation sensors and control system 100 for controlling combustion parameters associated with a gas turbine combustor 102, according to example embodiments of the invention. The interrogation sensor components may be placed or mounted adjacent to the can combustor 102 and may selectively interrogate regions within the can combustor 102, for example, at or near the air/fuel region 108, or within the post-flame (or exhaust) region 110 of the can combustor 102. FIG. 1 indicates two example placements and embodiments of the interrogation system, one near the air/fuel region 108 and one near the post flame region 110. One or more such systems may be placed at any suitable location within the combustor system without departing from the scope of the invention.

According to an example embodiment of the invention, a light source 111 under control of a light source controller 112 may generate light for interrogating the combustor. The generated light may propagate through an inner portion of the combustor 102 chamber via a series of optical components. According to an example embodiment, the light generated by the light source 111 may be coupled into a waveguide 114, such as an optical fiber, for convenient routing to an appropriate entry region of the combustor 102. According to an example embodiment, the light propagating out of the waveguide 114 may undergo divergence and may result in a spreading or diverging optical beam 117 that may be collimated by a lens 116 or concave mirror to produce a collimated optical beam 119. According to another example embodiment, the light produced by the light source (particularly if it is already collimated by the light source) may travel through free-space and may reach the appropriate entry region of the combustor 102 either directly, or via reflecting mirrors or intervening optics. The collimated optical beam 119 may enter the combustor 102 via an input optical port 118. The input optical port 118 and an output optical port 120 may be provided in the body of the turbine can combustor 102 to allow the optical energy to pass through the combustor 102. The input optical port 118 and an output optical port 120 may be constructed from high temperature-resistant, optically transparent material such as quartz, sapphire, or other suitable materials with low loss and a transmission bandwidth appropriate for the wavelengths of interest.

According to example embodiments of the invention, two or more optical ports 118 120 may be positioned on the combustor 102 at various locations for measuring combustion species at different points along the air/fuel-flame-exhaust path. According to example embodiments, the collimated light 119 propagating within the combustor 102 may interact with combustion species, and as a result of the path-averaged interaction with the species, may undergo wavelength-specific spectral attenuation that may correlate with the concentration of the particular chemical species within the combustor 102.

According to an example embodiment of the invention, the spectrally attenuated light exiting the combustor 102 through the output optical port 120 may pass through a lens 122 or concave mirror 124 to produce a converging optical beam 123 for sensing with one or more detectors 126. According to example embodiments of the invention, the optical detector(s) 126 may be selected for response within certain wavelength spectra windows of interest. For example, a silicon carbide (SiC) photo detector may be selected because of its sensitivity to the ultra violet portion of the wavelength spectrum. According to another embodiment, a silicon (Si) photo detector may be utilized for monitoring the emission from chemical species in the about 400 to about 1000 nm spectrum. According to another example embodiment, Indium gallium arsenide (InGaAs) photodiodes may be selected for measuring infra-red wavelengths in the about 1000 to about 1700 nm spectrum. The optical signals detected by the detectors 126 may be converted by the detectors 126 into electronic signals that may be further processed (filtered, amplified, etc.) by the detector electronics 128. The output electronic signals from the detector electronics 128 may be utilized by the combustor control system 130 to dynamically adjust combustor parameters (air/fuel ratios, fuel distribution, mass flow fuel nozzle acoustic impedance, air flow distribution, etc.) to optimize the parameters of the combustor.

Figure 2A:
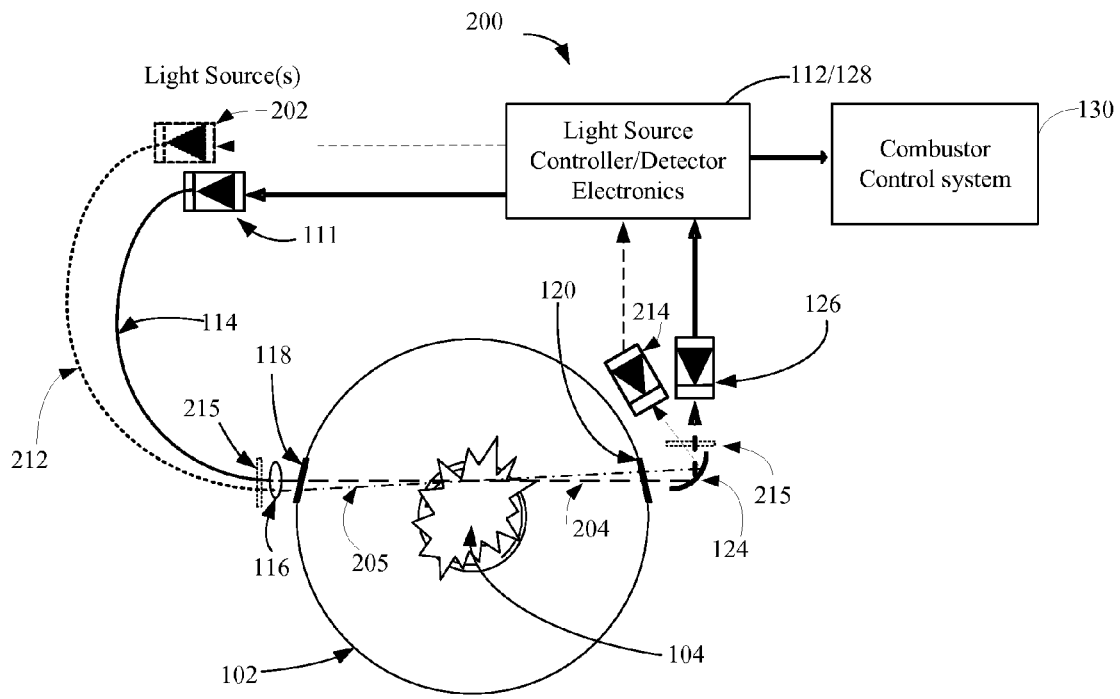
FIG. 2a illustrates an end view of a combustor and optical interrogation system, in accordance with an example embodiment of the invention.

FIG. 2*a* depicts an end view an optical interrogation system, in accordance with example embodiments of the invention, the light source emitter 111 may comprise a tunable laser. In another example embodiment, light source emitter 111 may be a fixed wavelength laser. In yet another example embodiment, light source emitters 111 202 may comprise multiple lasers or multiple line lasers. According to another example embodiment, the light source emitter 111 may comprise a wide-band light source such as an Amplified Stimulated Emission (ASE) source, supercontinuum source, or super luminescent light emitting diode (SLED).

Figure 2B:
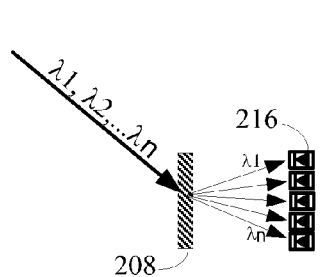
FIG. 2b illustrates a transmission diffraction grating and detector array for spatially separating wavelengths prior to detection, according to an example embodiment of the invention.
Figure 2C:
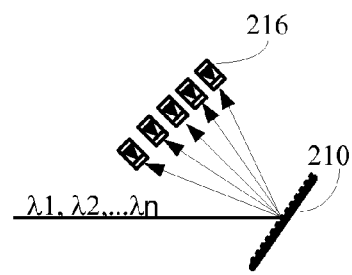
FIG. 2c illustrates a reflection diffraction grating and detector array for spatially separating wavelengths prior to detection, according to an example embodiment of the invention.

The design details of the measurement system for interrogating the chemical species within the combustor 102 may depend upon on the chemical species of interest, and may range in complexity from a single line laser light source 111, with a single detector 126, to a tunable laser or ASE source, with additional optical components to enable portions of the spectrum to be resolved and measured. Various example optical systems and detection schemes, according to example embodiments of the invention will now be discussed with reference to FIGS. 2*a-c*.

Basic Fixed Laser Interrogation Embodiments

According to one example embodiment, and as mentioned above, a single line laser or laser diode may be utilized as the light source 111. The narrowband emission from the laser may be adjusted to match an absorption band of a chemical species of interest. For example, H2O has absorption bands near 1.45 μm, 1.95 μm, and 2.5 μm; CH4 has a absorption band near 1.65 μm; CO has an absorption band near 1.55 μm; C2 has an absorption band near 518 nm; CH has an absorption band near 530 nm; OH has an absorption band near 310 nm, and NO has an absorption band near 226 nm. By matching the light source's 111 emission wavelength to one or more of these absorption wavelengths, and by selecting the proper optical detector 126, a ratio of input to output optical energy can be measured and correlated with the relative concentration of the combustion species of interest.

Multiple Laser Interrogation Embodiments

According to an example embodiment, multiple laser sources 111 202 and multiple corresponding detectors 126 214 may be utilized for measuring multiple combustion species simultaneously, or for more accurately measuring a single combustion species by employing normalizing methods, as will be described subsequently. In one example embodiment, one or more light sources 111 202 may couple into, and may be routed via corresponding optical waveguides 114 214 to a common lens 116 and input port 118, and may utilize co-linear (or roughly parallel) but spatially separated optical paths 204 205 and may exit a common output port 120 and may be detected with corresponding optical detectors 126 214 by virtue of the optical path separations or launch angles. In another example embodiment (not shown in FIG. 2a, but alluded to in FIG. 1) the multiple light sources may follow individual paths and may utilize dedicated optics (lenses, mirrors, input and output ports, detectors, etc.).

Tunable Laser Interrogation Embodiments

According to an example embodiment of the invention, the light source 202 may comprise a tunable laser capable of tuning over a spectrum of wavelengths. The tunable laser may enable measuring the absorption spectra of one or more chemical species within the combustor. According to example embodiments, and depicted in FIGS. 2b and 2c, a transmission regime grating 208 or reflection regime grating 210 may be utilized to angularly separate the spectral components ($\lambda 1, \lambda 2 \ldots \lambda n$) of the tuned laser light after it has travelled through and interacted with the chemical species within the combustor 102. The angularly separated light may then be resolved and detected by multiple (spatially separated) detectors in a detector array 216. The resulting detected signals may be sampled in time and related to the known tuning wavelength of the tunable laser to produce a combined representation of the chemical species' absorption spectra within the combustor 102. The measured absorption spectra may then be related to the relative concentrations of the chemical species of interest, and may be utilized for controlling the parameters of the combustor 102.

According to another example embodiment of the system employing a tunable laser, such as a chirped laser, a single detector may be utilized to measure the light that has passed through the combustor 102. By relating the tunable laser wavelength change with the detected signal in the time domain, the time-domain signal may be utilized to measure the absorption spectra of the chemical species within the combustor 112 over the wavelength band of interest without utilizing multiple detectors or gratings.

Wideband Light Source Interrogation Embodiments

According to example embodiments of the invention, the light source 202, may comprise a wideband optical source, such as an amplified stimulated emission (ASE) source, supercontinuum source, or super luminescent light emitting diode (SLED) source. In these embodiments, photons covering a spectrum of wavelengths within the emission bandwidth of the source may simultaneously interrogate the chemical species within the combustor 102 to produce a combined absorption spectra. According to example embodiments, and with reference to FIGS. 2b and 2c, a transmission grating 208 or reflection grating 210 may be utilized to angularly separate the spectral components ($\lambda 1, \lambda 2 \ldots \lambda n$) of the wideband light after it has travelled through and interacted with the chemical species within the combustor 102. The angularly separated light may then be resolved and detected by multiple (spatially separated) detectors in a detector array 216. The resulting detected signals may represent a combined chemical species' absorption spectra within the combustor 102. The measured absorption spectra may then be related to the relative concentrations of the chemical species of interest, and may be utilized for controlling the parameters of the combustor 102. According to another example embodiment, one or more optical filters 215, (dichroic, Fabry Perot, etc.) may be placed in the optical path to limit the measured spectrum to a wavelength band of interest. Pre- or post-combustor filtering of the light (prior to reaching the detector) may simplify the detector arrangement, and may serve to eliminate the need for a grating or multiple detectors. Placing a filter 215 over the detector may also be used to reduce unwanted stray light, for example, from the flame region. Many combinations and variations of the above-mentioned embodiments may be employed without departing from the scope of the invention. Therefore, it is to be understood that the invention is not to be limited to the specific embodiments disclosed.

Also shown in FIGS. 1 and 2a are blocks representing the detector electronics 128 and the combustion control system 130. According to an example embodiment, the detector electronics 128 may be operable to condition, amplify, filter, and process the signals from the optical detectors 126 214 216. The detector electronics 128 may also provide control for automatically adjusting the position of any of the corresponding optical components. The output signal from the detector electronics may be used as a control signal for the combustion control system 130. For example, according to an embodiment of the invention, the measured concentration of CH4, or the measured ratio of CH4 to CO2 may be utilized as feedback in the combustion control system 130, and may provide a control to dynamically adjust the fuel/air ratio.

Figure 3:
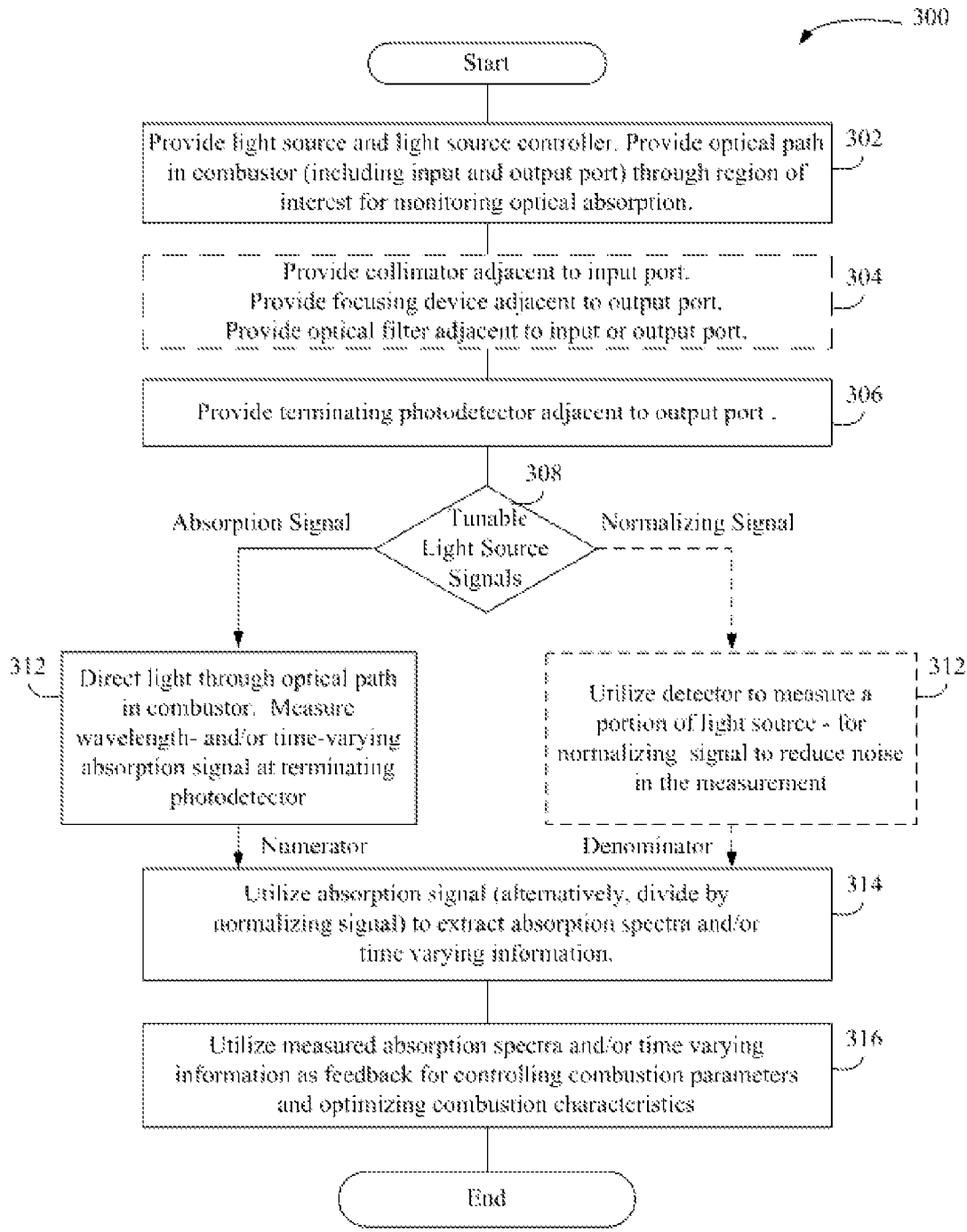
FIG. 3 is an example method flowchart for measuring absorption parameters within a turbine combustor, according to an example embodiment of the invention.

An example method for measuring chemical species within a combustor 102, and for controlling combustion characteristics based on the measurements will now be described with reference to the flowchart of FIG. 3. Beginning in block 302 and according to an example embodiment of the invention, a light source 111 and light source controller 112 may be provided. At least one optical path, including an optical input port 118 and output port 120, may be provided in the body of the turbine can combustor 102 adjacent to a region of interest 106 110 to allow light from the light source 111 to propagate through the combustor 102 for monitoring the chemical species present in the combustor 102 via optical absorption. The optical ports 118 120 may be constructed from high temperature resistant, optically transparent material such as quartz, sapphire, or other suitable materials with low loss and a transmission bandwidth appropriate for the wavelengths of interest. In optional block 304, a collimator 116 may be provided adjacent to the input port 118, if necessary, to correct any beam divergence of the light from the light source 111 and to collimate the beam 119. Adjacent to the output port 120, a focusing device may be provided to concentrate the modified light exiting the combustor 102. According to example embodiments, the focusing device may be a lens 122 or a concave mirror 124. In block 306, a terminating photodetector 126 may be provided adjacent to the output port 120 and may be operable to accept the focused or concentrated light 123 provided by the output lens 122 or mirror 124.

Blocks 308, 310, and 312 indicate that the absorption signal measurement may be normalized to increase the measurement accuracy and sensitivity by measuring the absorption signal and dividing by a normalizing signal. In block 312, according to an example embodiment, the normalizing signal may be produced by measuring a portion of the light from the light source 111 prior to the propagation of the light through the combustor 102. Such a signal may already be available at the light source controller 112 since the typical optical source controllers utilize an internal detector for monitoring the optical power of the light source 111 for feedback control. According to other example embodiments of the invention, the normalizing signal may be obtained using external light splitters and separate detectors (not shown) to capture and detect a portion of the light prior to propagating through the combustor 102. Block 310 indicates that the absorption signal is obtained by directing light through the optical path in the combustor 102, and by measuring the wavelength-varying and/or time-varying absorption signal at one or terminating photodetectors 126 214 216. Block 312 indicates that the normalized measurement signal may be obtained by dividing the absorption signal (numerator) by the normalizing signal (denominator). According to an example embodiment, since the normalizing method may be optional, if the absorption signal is not normalized, then the denominator can be set to 1.

In block 316, the extracted absorption spectra and/or time varying measurement information may be utilized to control and optimize the combustion characteristics of the combustor 102. For example, the extracted combustion parameters may be utilized in a feedback control loop for adjusting the fuel flow, fuel-to-air ratio, fuel distribution among the burners, etc.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of any appended claims. Although specific terms are employed herein, they are used in a generic and descriptive sense only and not for purposes of limitation.

The claimed invention is:

1. A method for controlling combustion parameters associated with a gas turbine combustor, the method comprising:
    providing an optical path through a combustion region of the gas turbine combustor, the optical path comprising at least one photodetector;
    propagating light along the optical path;
    measuring absorption of light at a plurality of different points of the optical path within the combustion region via the at least one photodetector; and
    controlling at least one of the combustion parameters based at least in part on the measured absorption of light at the plurality of different points.

2. The method of claim 1, wherein providing an optical path comprises providing an input optical port and an output optical port.

3. The method of claim 1, wherein propagating light along the optical path comprises providing a light source, an optical waveguide, and a collimator for directing light from the light source along the optical path.

4. The method of claim 1, wherein propagating light along the optical path comprises providing at least one grating or filter for separating spectral information associated with the light.

5. The method of claim 1, wherein propagating light along the optical path comprises propagating narrow-band optical radiation for measurement of absorption.

6. The method of claim 5, wherein propagating light along the optical path comprises propagating light tunable within a wavelength range between about 225 nanometers to about 3 microns for measurement of an absorption spectrum.

7. The method of claim 1, wherein propagating light along the optical path comprises propagating wide-band optical radiation for measurement of an absorption spectrum.

8. The method of claim 1, further comprising: measuring at least one normalizing signal associated with a portion of the light; and measuring absorption of the light within the gas turbine combustor based at least in part on the at least one normalizing signal.

9. The method of claim 8, further comprising: controlling at least one of the combustion parameters based at least in part on the measured absorption and the at least one normalizing signal.

10. The method of claim 1, wherein the combustion parameters comprise at least one of: fuel flow rate, fuel flow distribution, or air/fuel ratio.

11. A system for controlling combustion parameters associated with a gas turbine combustor, the system comprising:
    at least one photodetector in communication with an optical path through a combustion region of the gas turbine combustor, the at least one photodetector being configured to measure absorption of light at a plurality of different points along the optical path;
    at least one light source operable to propagate light along the optical path to the at least one photodetector; and
    a control device operable to control at least one of the combustion parameters based at least in part on one or more signals from the one or more photodetectors.

12. The system of claim 11, wherein the optical path comprises an input optical port, and an output optical port.

13. The system of claim 11, wherein the optical path comprises an optical waveguide and a collimator for directing light from the at least one light source along the optical path.

14. The system of claim 11, wherein the optical path comprises at least one grating or filter for separating spectral information associated with the light.

15. The system of claim 11, wherein the at least one light source comprises a narrow-band optical radiation source for measurement of absorption.

16. The system of claim 11, wherein the at least one light source comprises a tunable light source with a wavelength range between about 225 nanometers and about 3 microns for measurement of an absorption spectrum.

17. The system of claim 11, wherein the at least one light source comprises a wide-band optical radiation source for measurement of an absorption spectrum.

18. The system of claim 11, further comprising: one or more photodetectors operable to measure at least one normalizing signal associated with the at least one light source; one or more photodetectors operable to measure absorption of the light within the gas turbine combustor based at least in part on the at least one normalizing signal.

19. The system of claim 18, further comprising: at least one control device operable to control at least one of the combustion parameters based at least in part on the measured absorption and the at least one normalizing signal.

20. A gas turbine comprising:
   a combustor comprising an optical path;
   at least one photodetector in communication with the optical path through a combustion region of the gas turbine combustor, the at least one photodetector being configured to measure absorption of light at a plurality of different points along the optical path to generate one or more absorption signals;
   at least one light source operable to propagate light along the optical path to the at least one photodetector; and
   at least one control device operable to control one or more combustion parameters based at least in part on the one or more absorption signals from the at least one photodetector.

* * * * *